| United States Patent [19] | [11] | 4,427,655 |
|---|---|---|
| Stapley | [45] | Jan. 24, 1984 |

[54] ANTIBIOTICS-875A AND PRODUCTION THEREOF

[75] Inventor: Edward O. Stapley, Metuchen, N.J.

[73] Assignee: Merck & Co., Inc., Rahway, N.J.

[21] Appl. No.: 367,529

[22] Filed: Apr. 12, 1982

[51] Int. Cl.$^3$ .................. A61K 35/00; C12P 1/06
[52] U.S. Cl. ..................................... 424/115; 435/169
[58] Field of Search ........................ 424/115; 435/169

[56] References Cited

U.S. PATENT DOCUMENTS 4,180,564 12/1979 Godfrey et al. ................... 424/117

*Primary Examiner*—Jerome D. Goldberg
*Attorney, Agent, or Firm*—Raymond M. Speer; Ernest V. Linek; Hesna J. Pfeiffer

[57] ABSTRACT

The Antibiotics-875A are obtained from the controlled aerobic cultivation of *Streptomyces hygroscopicus* ATCC 39067. The Antibiotics-875A show in vitro and in vivo activity against gram positive and gram negative organisms including the genera; Staphylococcus, Streptococcus, Aerobacter, Escherichia, Klebsiella, Parlacolobactrum, Pseudomonas and Salmonella.

6 Claims, No Drawings

ANTIBIOTICS-875A AND PRODUCTION THEREOF

BACKGROUND OF THE INVENTION

The present invention is directed toward the Antibiotics-875A and the production thereof.

In particular, the present invention relates to the novel Antibiotics-875A, having antibacterial activity, especially against *Pseudomonas aeruginosa*, and to a method for producing the Antibiotics-875A, characterized by cultivating an Antibiotics-875 producing strain of *Streptomyces hygroscopicus* in an aqueous nutrient medium under aerobic conditions and isolating the accumulated Antibiotics-875A from the culture broth.

The microorganism, *Streptomyces hydroscopicus* has been deposited without restriction in, and made a part of the American Type Culture Collection, Rockville, Md., from which it is available under accession No. ATCC 39067.

The Antibiotics-875A are different from other known antibiotics. The only antibiotic mixture that is similar in activity and composition is A-38533 which is fully described in Godfrey et al., U.S. Pat. No. 4,180,564.

SUMMARY OF THE INVENTION

There is thus provided the novel Antibiotics-875A and a method of producing said mixture of antibiotics which comprises cultivating *Streptomyces hygroscopicus* ATCC 39067 under controlled aerobic conditions in an aqueous nutrient medium at a temperature range of 22° C. to 30° C. for about 24 to 200 hours and isolating the accumulated Antibiotics-875A from the cultured broth.

DETAILED DESCRIPTION OF THE INVENTION

As used herein, the term "Antibiotics-875A" is defined as a mixture including those antibacterial active components produced by cultivating *Streptomyces hygroscopicus* ATCC 39067 under the conditions set forth in the instant application. These active components include, but are not limited to those designated herein as: 875A1, 975A2, 875A3, 875A4, and 875A5. As will be recognized by those artisans skilled in the fermentation arts, the number and ratio of the individual Antibiotics-875A components will vary, depending upon the fermentation conditions, and the strain used.

It is to be understood that for the production of Antibiotics-875A, the present invention is not limited to the use of *Streptomyces hygroscopicus* ATCC 39067. It is especially desired and intended to include the use of natural or artificial mutants produced from the described organism, or other variants of *Streptomyces hydroscopicus* ATCC 39067 as far as they can produce the Antibiotics-875A. The artificial production of mutant *Streptomyces hygroscopicus* may be achieved by a conventional operation such as X-ray or ultraviolet (UV) radiation, or by the use of chemical mutagens such as; nitrogen mustards, nitrosoguanidine, camphor and the like.

MORPHOLOGICAL AND CULTURAL CHARACTERISTICS OF STREPTOMYCES HYGROSCOPICUS ATCC 39067

The cultural and morphological characteristics described herein have been compared to those descriptions of Streptomyces species in Bergey's *Manual of Determinative Bacteriology*, 8th edition, the Williams and Wilkins Co.; E. B. Shirling and D. Gottlieb's "Cooperative Descriptions of Type Cultures of Streptomyces", *Inst. J. Syst. Bact.* 18, 69–189, 279–399 (1968); and S. A. Waksman *The Antinomycetes*, Vol. 2, 1961, The Williams and Wilkins Co. These comparisons show that the culture ATCC No. 39067 has the major species-defining characteristics of *Streptomyces hygroscopicus*. Differences are minor and of a strain differentiating nature.

The cultural characteristics of the Antibiotic-875A producing strain, *Streptomyces hygroscopicus* ATCC 39067 are as follows:

(V = vegetative growth; A = aerial mycelium; SP = soluble pigment)

Morphology: Sporophores form very compact spirals, clustering along main hyphae. On salts-starch agar, spirals coalesce to become dark moist areas in the aerial mycelium. Spore surface (electron microscope)—smooth with many having an irregular, roughened appearance.

Oatmeal agar (ISP Medium 3)
  V: Reverse—brown
  A: Dark brownish-gray, velvety
  SP: None
Czapek Dox agar (sucrose nitrate agar)
  V: Reverse—dark tan to brown
  A: Drab gray mixed with white
  SP: Light brown
Egg albumin agar
  V: Tan
  A: Sparse—grayish
  Sp: None
Glycerol asparagine agar (ISP Medium 5)
  V: Reverse—grayish tan
  A: Dark brownish-gray mixed with light gray and white non-sporulating areas
  SP: None
Inorganic salts-starch agar (ISP Medium 4)
  V: Reverse—grayish cream
  A: Brownish-gray mixed with white non-sporulating areas. Dark moist areas develop after 10–14 days.
  SP: None
Yeast extract-dextrose+salts agar
  V: Reverse—tan
  A: Light gray mixed with white
  SP: None
Yeast extract-malt extract agar (ISP Medium 2)
  V: Reverse—yellow tan
  A: Light gray mixed with white
  SP: None
Peptone-iron-yeast extract agar
  V: Tan
  A: Sparse, whitish
  SP: None
  Melanin: None
  $H_2S$ production: None
Nutrient agar
  V: Cream-colored
  A: Moderate, white
  SP: None
Nutrient starch agar
  V: Cream-colored
  A: Moderate, white
  SP: None
  Hydrolysis of starch—Good
Nutrient gelatin agar
  V: Cream-colored to tan
  A: Moderate, white SP: None
Liquefaction of gelatin—moderate
Geltain stabs
  V: Tan
  A: None
  SP: None
  Liquefaction of gelatin—moderate
Skim milk agar
  V: Tan
  A: Moderate, grayish-white
  SP: Slight browning of medium
  Hydolysis of casein: Good
Litmus milk
  V: Tan growth ring
  A: None
  Color: lavender-blue
  Coagulation and/or peptonization: Partial peptonization, becoming slightly alkaline
Skim milk
  V: Tan growth ring
  A: None
  SP: None
  Coagulation and/or peptonization: Partial peptonizkation, becoming slightly alkaline
Potato plug
  V: Brown
  A: Sparse, grayish white
  SP: Slight browning of medium
Loeffler's Blood serum
  V: Tan
  A: None
  SP: Slight browning of medium
  Liquefaction: Moderate
Nutrient tyrosine agar
  V: Tan
  A: Moderate, white
  SP: Slight browning of medium
  Decomposition of tyrosine: Positive
Carbon utilization:

| Pridham-Gottlieb basal medium + 1% carbon source; + = growth; ± = growth poor or questionable; − = no growth as compared to negative control (no carbon source) | |
|---|---|
| Glucose | + |
| Arabinose | − |
| Cellulose | − |
| Fructose | + |
| Inositol | + |
| Lactose | + |
| Maltose | + |
| Mannitol | + |
| Mannose | + |
| Raffinose | + |
| Rhamnose | − |
| Sucrose | + |
| Xylose | + |

Temperature range: (Yeast extract-dextrose+salts agar)
28° C.—Good vegetative and aerial growth
37° C.—Vegetative growth but no aerial hyphae
50° C.—No growth
Oxygen requirement: (Stab culture in yeast extract-dextrose+salts agar)
Aerobic
All readings were taken after three weeks at 28° C. unless noted otherwise. The pH of all media was approximately neutral (6.8–7.2).

In the present invention, the new Antibiotics-875A are produced during cultivation of the microorganism, for example, *Streptomyces hygroscopicus* ATCC 39067 at a temperature of about 22° C. to 30° C., preferably 24° C., under aerobic conditions. The composition of the nutrient medium may be varied over a wide range. The essential assimilable nutrient ingredients are; a carbon source, a nitrogen source, source of inorganic elements including phosphate, sulfur, magnesium, potassium, calcium and chlorine. Cultivation is most productive under from neutral to alkaline pH conditions, preferably from about 7.5 to 8.8.

Typical sources of carbon include, glucose, dextrin, starches, glycerol and the like. Typical nitrogen sources include vegetable meals (soy, cottonseed, corn, etc), meat flours or animal peptones, distillers solubles, casamino acids, yeast cells, various hydrolysates (casein, yeast, soybean, etc.), yeast nucleic acids and amino acids.

Mineral salts such as the chlorides, nitrates, sulfates, carbonates and phosphates of sodium, potassium, ammonium, magnesium and calcium provide a source of essential inorganic elements. The nutritive medium may also contain a number of trace elements such as iron, copper, manganese, zinc and cobalt.

If excessive foaming is encountered during the cultivation, antifoaming agents such as vegetable oils, lard oil and polypropylene glycol may be added to the fermentation medium prior to, or during the course of the fermentation. The maximum yield of the Antibiotics-875A can be achieved within from about 48 to 200 hours, usually in about 100 hours, of fermentation under optimum conditions of temperature and aeration. The inoculum for the fermentation can be provided from suspensions, frozen cells or freeze-dried preparations.

ISOLATION OF THE ANTIBIOTICS-875A

After cultivation, the Antibiotics-875A can be recovered from the cultured broth by conventional means. Generally, the whole broth is filtered and then acidified to about pH 3.5 using a mineral acid, for example, 2.5 N hydrochloric acid. The acidified broth is admixed with a cationic ion exchange resin such as, Dowex 50×4 sodium cycle resin of from 20 to 50 mesh particle size. After mixing about 1 hour, the resin is separated from the broth.

The resin is stirred with water and large particle broth solids are floated out. The washed resin is transferred to a column and eluted with 5 bed volumes of 0.2 N ammonium hydroxide. The eluate is concentrated in vacuo to about 1/40 the broth volume and adjusted to from pH 6.5 to 7.5 with 2.5 N hydrochloric acid.

The individual components of the Antibiotics-875A complex are isolated from this concentrated or "enriched" broth.

The enriched broth is adsorbed on a 1 liter bed of a non-polar adsorbent polystyrene resin such as, XAD-2 resin (Rohm & Haas Co.) and washed with 1 liter water. The XAD-2 resin is then eluted with 10 bed volumes of 10% methanol-water (v/v). This eluate is concentrated in vacuo to about 500 ml and lyophylized. The isolated product is crude Antibiotic-875A1. Crude 875A1 is shown by further chromatographic purification to comprise Antibiotics-875A1, 875A2 and 875A4.

The crude 875A1 material may be further purified by chromatography on a cationic ion exchange resin such as, Dowex 50×4, 400 mesh resin in a pH 8.0 phosphate buffer containing 0.5 N Na⁺ and 0.5% (v/v) benzyl alcohol. Under these conditions, the three components were recovered; 875A1 at 7.1 displacement volumes, 875A2 at 10.8 displacement volumes; and 875A4 at 17.3 displacement volumes. A displacement volume is defined as the volume of liquid within a column bed volume but external to the solid phase itself.

The XAD-2 resin remaining after isolation of the crude Antibiotic-875A1 is next eluted with 80% methanol-water (v/v). The total eluate is about 5 displacement volumes. This eluate is concentrated in vacuo to about 500 ml and lyophilized. The isolated product is crude Antibiotic-875A3.

The crude Antibiotic-875A3 is shown by further chromatographic purification to comprise Antibiotics-875A3 and 875A5.

The crude 875A3 material may be further purified on a gel filtration medium such as, SE Sephadex C-25 resin (Pharmacia Fine Chemicals, Inc.), using pH 5.25 sodium acetate 0.1 N in Na+. Elution with 7 displacement volumes isolated the major component, 875A3 and 42 displacement volumes recovered the minor componenet 875A5.

CHARACTERIZATION OF ANTIBIOTICS-875A

All five components of Antibiotics-875A have the same U.V. adsorption curve; λmax. 262 nm, which is unshifted with a change in pH.

Acid hydrolysis with 6 N HCl at 100° C. for 18 hours yields uracil, as identified by U.V. and proton NMR analysis. $NH_3$ and erythro β-hydroxyleucine are detected by automatic amino acid analyses.

Paper electrophoresis with a pH 7.0 phosphate buffer at 600 volts D.C. for 3 hours shows no movement for components A3 and A5. Components A1, A2 and A4 all move in a similar manner toward the cathode. Using a pH 10.0 carbonate buffer at 600 volts D.C. for 3 hours; all five components exhibit similar mobility toward the anode.

Thin layer chromatography using an elution system of isopropanol-formic acid-water (4:1:1) on cellulose plates resolves component A1 from A2 and A4. A1 has Rf=0.37 and components A2 and A4 have $R_f$=0.48. Detection is by florescence.

ANTIBIOTIC ACTIVITY

Production of the Antibiotics-875A may be followed during the fermentation by testing a sample of the broth for antibiotic activity. Two assay organisms useful in testing these antibiotics are *Pseudomonas stutzeri* and *Klebsiella pneumoniae*. Assays are run using ½" paper discs dipped into the supernatant of a centrifuged aliquot of broth. The plates are incubated at 37° C. for 18–24 hours before the zones of inhibition are measured.

Antibiotic activity is generally present after 24 hours and remains present for at least 8 days during the fermentation. Peak antibiotic production occurs at from 4 to 7 days fermentation time.

The Antibiotics-875A components exhibit a wide range of in vitro activities against pathogenic organisms. The in vitro activity of the components of Antibiotics-875A are shown in Table I.

TABLE I

875A In Vitro Activity

| Organism | Inhib. Zone Diam., mm. at 250 μg/ml | | | | | | | |
|---|---|---|---|---|---|---|---|---|
|  | A1 | A2 | A3 | A4 | A5 | A6 | A7 | A8 |
| Bacillus | 0 | 0 | 0 | 0 | 0 | 0 | 0 | 7 |
| *Pseudomonas aeruginosa* | 0 | 0 | 0 | 0 | 0 | 0 | 0 | 0 |
| *Staphylococcus aureus* | 0 | 0 | 0 | 0 | 0 | 0 | 0 | 6 |
| *Bacillus subtilis* | 0 | 0 | 0 | 0 | 0 | 0 | 0 | 7 |
| *Staphylococcus aureus* | 0 | 0 | 20 | 0 | 0 | 0 | 0 | 0 |
| *Alcaligenes faecalis* | 0 | 0 | 14 | 0 | 0 | 0 | NT | NT |
| *Salmonella gallinarum* | 0 | 0 | 0 | 0 | 9 | 0 | 0 | 0 |
| *Vibrio percolans* | 0 | 0 | 0 | 0 | 11 | 0 | 0 | 0 |
| *Proteus vulgaris* | 0 | 0 | 0 | 0 | 0 | 0 | 0 | 0 |
| *Escherichia coli* | 24 | 22 | 0 | 0 | 27 | 0 | 8 | 0 |
| *Pseudomonas stutzeri* | 14 | 14 | 0 | 0 | 40 | 22 | 22 | 21 |
| *Klebsiella pneumoniae* | 33 | 32 | 16 | 24 | 26 | 0 | 24 | 21 |
| *Aerobacter aerogenes* | 0 | 0 | 0 | 23 | 21 | 0 | 0 | 0 |
| *Erwinia atroseptica* | 0 | 0 | 0 | 40 | 14 | 0 | 0 | 0 |
| *Pseudomonas aeruginosa* | 0 | 0 | 0 | 0 | 10 | 0 | 0 | 0 |
| *Escherichia coli* | 0 | 0 | 0 | 20 | 18 | 0 | 0 | 0 |
| *Streptococcus agalactiae* | 0 | 0 | 0 | 0 | 0 | 0 | 9 | 0 |
| *Bacillus subtilis* in Chem. Defined Agar | 10 | 0 | 0 | 0 | 22 | 0 | 0 | 0 |
| *Staphylococcus aureus* in Chem. Defined Agar | 0 | 0 | 0 | 12 | 12 | 0 | 0 | 0 |
| *Micrococcus flavus* | 0 | 0 | 0 | 0 | 0 | 12 | 0 | 0 |
| *Staphylococcus aureus* | 0 | 0 | 0 | 0 | 0 | 0 | 15 | 12 |

NOTE: NT means not tested.

The Antibiotics-875A exhibit a broad spectrum of in vivo activity. The Antibiotics have protected mice against infection with three strains of gram positive organisms representing two genera (Staphylococcus and Streptococcus) and 20 strains representing six genera of gram negative organisms (Aerobacter, Escherichia, Klebsiella, Parlacolobactrum, Pseudomonas and Salmonella.) At the concentrations tested there was no activity against any of three strains of Proteus, nor against one strain each of Pasteurella or Serratia. Tables II, III and IV summarize more in vivo activity results.

Although the majority of in vivo tests used the intraperitoneal (ip) route of therapy, activity has also been demonstrated when treatment was given via the subcutaneous route (sc).

TABLE II

IN VIVO ACTIVITY DATA

| Test Organism | Route of Therapy | Fraction of 875A[a] $ED_{50}$ in μg × 2 doses | | |
|---|---|---|---|---|
|  |  | A1 | A2 | A3 |
| *Klebsiella pneumoniae* | ip[b] | 24 | 24 | 13 |
|  | sc[b] | 53 | 27 | 43 |
| *Pseudomonas aeruginosa* | ip | 222 | 854 | 431 |
|  | sc | 4000 | 4000 | 4000 |
| *Salmonella schottmuelleri* | ip | 151 | 151 | 250 |
|  | sc | 2000 | 500 | 1300 |

[a]Amount of compound per ml reported to produce a 25 mm zone against *Klebsiella pneumoniae*, i.e. A1: 5 μg; A3: 30 μg; A3: 4 μg
[b]ip - intraperitoneal, sc - subcutaneous

TABLE III

IN VIVO DATA FOR 875- A1, A2, A3 and A4

| Antibiotic 875- | In Vitro Potency[a] | $ED_{50}$ Against *K. pneumoniae*[b] μg × 2 Doses | |
|---|---|---|---|
|  |  | ip | sc |
| A1 | 5.0 | 67 | 47 |
| A2 | 5.4 | 43 | 83 |
| A3 | 30 | 27 | 70 |

TABLE III-continued

IN VIVO DATA FOR 875- A1, A2, A3 and A4

| Antibiotic 875- | In Vitro Potency[a] | ED$_{50}$ Against K. pneumoniae[b] μg × 2 Doses | |
|---|---|---|---|
| | | ip | sc |
| A4 | 2.4 | 89 | 165 |

[a]Amount of compound per ml reported to produce a 25 mm zone against *Klebsiella pneumoniae*.
[b]Infection intraperitoneally with 100 LD$_{50}$ doses of *Klebsiella pneumoniae* given in broth. Therapy by the indicated route at the time of infection and again 6 hours later.

TABLE IV

Effect of Dosage Schedule on 875A1 Therapy of *Pseudomonas aeruginosa*

| Number of Treatments | Hour After Infection | Route of Therapy | ED$_{50}$ in μg/dose | |
|---|---|---|---|---|
| | | | Test 1 | Test 2 |
| 2 | 0 & 6 | ip | 36 | 1,300 |
| | | sc | 20,000 | 20,000 |
| 3 | 0, 2 & 6 | ip | 151 | 1,700 |
| | | sc | 20,000 | 20,000 |
| 4 | 0, ½, 2 & 5 | ip | 250 | 1,000 |
| | | sc | 13,300 | 20,000[a] |

[a]Significance of prolongation of survival time (p/ = 0.005).

From the foregoing in vitro and in vivo data it is expected that an effective antibacterial amount of the Antibiotics-875A would be on the order of 0.6 mg/kg to 43 mg/kg in mammals. The Antibiotics-875A are effective for treatment of gram negative and gram positive infections as described above, and may be administered i.v. or s.c., either alone or in combination with a pharmaceutical carrier. The ultimate choice of route and dose should be made by an attending physician and based upon the patient's unique condition.

Combinations of Antibiotics with appropriate pharmaceutical carriers are accomplished by methods well known to the pharmacist's art. For purposes of subcutaneous (s.c.) administration, solutions of the antibiotic are generally employed, for example, sterile aqueous or alcoholic solutions. Such solutions should be suitably buffered if necessary and the liquid diluent may first be rendered isotonic with saline or glucose. These aqueous and alcoholic solutions are also suitable for intravenous (i.v.) injections.

The following examples illustrate the preparation of the Antibiotics-875A from *Streptomyces hygroscopicus* ATCC 39067.

For Examples I–III, the following table (Table V) describes the various nutrient media used. For convenience, the media will be referred to in the examples as described below.

TABLE V

| Medium A | | *Phosphate Buffer Solution | |
|---|---|---|---|
| Ardamine (Autolysed Yeast) (From Yeast Products, Inc.) | 10.0 g | | |
| Glucose (Reagent Grade) | 10.0 g | KH$_2$PO$_4$ | 91.0 g |
| *Phosphate Buffer | 2.0 ml | Na$_2$HPO$_4$ | 95.0 g |
| MgSO$_4$ 7H$_2$O | 0.05 g | Distilled H$_2$O | 1000 ml |
| Distilled H$_2$O | 1000 ml | pH 7.0 | | pH: Adjust to 6.5 using NaOH
Seed Flasks: Dispense 50 ml per 250 ml baffled Erlenmeyer flask, cottonplug, autoclave at 120° C. for 20 minutes.
Slants: Add Difco agar at 25.0 g/l before sterilization; dispense 14 ml per 22 × 175 mm culture tube, cotton-plug, autoclave at 120° C. for 15 minutes, and slant the tubes while the agar is solidifying.

Medium B

| | |
|---|---|
| Amber Yeast BYF 300 (Amber Labs., Inc.) | 10.0 g |
| Distiller's Solubles | 20.0 g |
| Glucose | 10.0 g |
| CaCO$_3$ | 3.0 g |
| Distilled H$_2$O | 1000 ml | pH: Adjust to 7.0 using NaOH
Dispense 250 ml medium per 2L unbaffled Erlenmeyer flask, cotton-plug, and autoclave at 120° C. for 25 minutes.

Medium C

| | |
|---|---|
| Glucose | 10.0 g |
| Primary Yeast NF (Yeast Products, Inc.) | 10.0 g |
| Distiller's Solubles | 25.0 g |
| NZ amine; type E (Sheffield Chemical) | 5.0 g |
| Polyglycol β 2000 (Dow Chemical Co.) | 0.25% by Volume |
| Distilled H$_2$O | 1000 ml | pH: Adjust to 7.2 using NaOH

| Medium | D | E |
|---|---|---|
| Glucose (Reagent Grade) | 10.0 g | 10.0 g |
| L-Lysine | 0.5 g | 0.5 g |
| DL-tryptophan | 1.0 g | 1.0 g |
| L-Asparagine | 1.0 g | 1.0 g |
| Aspartic Acid | 1.0 g | 1.0 g |
| DL-Isoleucine | — | 1.0 g |
| DL-threonine | 1.0 g | 1.0 g |
| MgSO$_4$.7H$_2$O | 0.5 g | 0.5 g |
| FeSO$_4$.7H$_2$O | 0.01 g | 0.01 g |
| ZnSO$_4$.7H$_2$O | 0.005 g | 0.005 g |
| K$_2$HPO$_4$ | 0.1 g | 0.1 g |
| CaCO$_3$ | 2.0 g | 3.0 g |
| Distilled H$_2$O | 1000 ml | 1000 ml | pH: Adjust to 7.3 using NaOH
Medium D: Dispense 50 ml per 250 ml baffled Erlenmeyer flask.
Medium E: Add 2 drops polyglycol 2000 per 250 ml Erlenmeyer flask and add 40 ml medium.
Cotton plug flasks and autoclave at 120° C. for 20 minutes

EXAMPLE I

A medium A slant (see Table V) of *Streptomyces hygroscopicus* ATCC 39067 was used to inoculate, using aseptic techniques, 3 seed flasks of medium A. These flasks were shaken at 28° C. on a 220 RPM shaker (2" throw) for 3 days at which time good growth was obtained. The broth from the 3 flasks was pooled aseptically and used to inoculate 12 production flasks. These flasks contained 250 ml medium B per 2L unbaffled Erlenmeyer flask and were inoculated using 7 ml seed broth per flask. The production flasks were shaken at 28° C. on a 220 RPM shaker for 4 days at which time they were harvested. Assays were run using ¼" discs dipped into the supernatant of a centrifuged aliquot of the harvested broth. These moistened discs were deposited on the surface of assay plates. Two assay organisms were used; *Pseudomonas stutzeri* and *Klebsiella pneumoniae*. These plates were incubated at 37° C. for 18–24 hours before the zones of inhibition were read. This batch gave zones (mm diameter) of 21/25 (ring) against *P. stutzeri* and 26/35 (hazy) against *K. pneumoniae*. The outer zone of a double ring zone was taken as the measure of potency.

EXAMPLE II

Streptomyces hygroscopicus ATCC 39067 was streaked onto agar plates so as to obtain single colony isolates. Medium A slants inoculated from the original slants were incubated at 28° C. for 1 week and used to prepare the lyophilized tubes employed in Example III. In addition, a medium A seed flask was inoculated from the original slant and, when the culture was grown, it was used to prepare vegetative vials, which were stored, frozen in nitrogen (vapor phase) until used. One of these vials was melted and the contents transferred aseptically to a medium A seed flask. This flask was grown for 1 day at 28° C. on a 220 RPM shaker at which time good growth was obtained. A second stage medium A seed flask was inoculated from this flask using 2.5 ml (5% inoculum) and shaken at 28° C. for 1 day. This second stage flask was used to inoculate 21×250 ml Erlenmeyer flask each containing 40 ml of medium C. These flasks were shaken at 24° C. for 5 days on a 220 RPM shaker at which time the contents of 20 flasks were pooled and assayed. A 1:10 dilution of the supernatant of a centrifuged aliquot of the harvested broth gave a 26/35 (hazy) mm zone of inhibition against *Klebsiella pneumoniae.*

EXAMPLE III

A frozen vegetative vial of *Streptomyces hydroscopicus* ATCC 39067 as described in Example II, was used to inoculate a seed flask of medium D which was shaken at 28° C. on a 220 RPM shaker for 3 days. This seed inoculum was used to inoculate 2 production flasks of medium E which were shaken at 24° C. on a 220 RPM shaker for 7 days with assays run at 6 and 7 days ages. Assays were run using ⅜" assay discs dipped in a 1:10 dilution of the supernatant of centrifuged broth. Against *Klebsiella pneumoniae*, the zone of inhibition was 28 mm at 6 days and 28.5 mm at 7 days age. Against *Pseudomonas stutzeri*, the zones were 22 mm at 6 days and 24 mm at 7 days age.

Claims of the invention to follow.
What is claimed is:

1. Antibiotics-875A which have the following characteristics:
   (a) U.V. Max. 262 nm unshifted by pH change (acidic/neutral/basic),
   (b) Acid hydrolysis (6 N HCl at 100° C. for 18 hr) yields uracil,
   (c) Paper electrophoresis with pH 7.0 phosphate buffer at 600 volts (D.C.) for 3 hours shows:
   875A1—Movement toward cathode
   875A2—Movement toward cathode
   875A4—Movement toward cathode
   875A3—No movement
   875A5—No movement
   (d) Paper electrophoresis with pH 10.0 carbonate buffer to 600 volts (D.C.) for 3 hours shows: 875A1 to 875A5—all move toward anode with same mobility
   (e) TLC data using isopropanol-formic acid-water (4:1:1) and cellulose plates—detection by flourescence shows:
   875A1: Rf=0.37
   875A2 & A4: Rf=0.48 prepared by the process of cultivating *Streptomyces hygroscopicus* ATCC 39067 under controlled aerobic conditions in an aqueous nutrient medium at a temperature range of about 22° C. to 30° C. for at least 24 hours at a pH of from 7.5 to 8.8.

2. A process for producing the Antibiotics-875A of claim 1 which comprises cultivating *Streptomyces hygroscopicus* ATCC 39067 under controlled aerobic conditions in an aqueous nutrient medium at a temperature range of about 22° C. to 30° C. for at least 24 hours at a pH of from 7.5 to 8.8.

3. The process of claim 2 wherein the accumulated Antibiotics-875A compounds produced are isolated from the cultured broth.

4. The process of claim 3 wherein the isolation of the Antibiotics-875A is accomplished by:
   (a) filtering the cultured broth and
   (b) employing chromatographic means to separate the Antibiotics-875A mixture of compounds.

5. A pharmaceutical composition for inhibiting the growth of gram negative and gram positive microorganisms, said composition comprising an antibacterially effective amount of the Antibiotics-875A of claim 1 and a pharmaceutical carrier.

6. A method of treating gram negative or gram positive infections in mammals which comprises intravenously or subcutaneously administering to said mammal an antibacterially effective amount of the Antibiotic-875A of claim 1 in pharmaceutical carrier.

* * * * *